(12) United States Patent
Nita et al.

(10) Patent No.: US 8,668,709 B2
(45) Date of Patent: Mar. 11, 2014

(54) STEERABLE ULTRASOUND CATHETER (75) Inventors: Henry Nita, Redwood City, CA (US); Jeff Sarge, Fremont, CA (US)

(73) Assignee: Flowcardia, Inc., Sunnyvale, CA (US)

( * ) Notice: Subject to any disclaimer, the term of this patent is extended or adjusted under 35 U.S.C. 154(b) by 688 days.

(21) Appl. No.: 12/036,870

(22) Filed: Feb. 25, 2008

(65) Prior Publication Data
US 2008/0172067 A1    Jul. 17, 2008

Related U.S. Application Data

(62) Division of application No. 10/722,209, filed on Nov. 24, 2003, now Pat. No. 7,335,180.

(51) Int. Cl.
*A61B 17/32* (2006.01)
*A61B 5/00* (2006.01)

(52) U.S. Cl.
USPC .......................... 606/169; 600/439; 600/585

(58) Field of Classification Search
USPC .......... 606/159, 169–171; 600/437, 439, 459, 600/466, 467, 585
See application file for complete search history.

(56) References Cited

U.S. PATENT DOCUMENTS

| | | |
|---|---|---|
| 3,433,226 A | 3/1969 | Boyd |
| 3,565,062 A | 2/1971 | Kuris |
| 3,631,848 A | 1/1972 | Muller |
| 3,719,737 A | 3/1973 | Vaillancourt et al. |
| 3,823,717 A | 7/1974 | Pohlman et al. |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance |
| 4,417,578 A | 11/1983 | Banko |
| 4,425,115 A | 1/1984 | Wuchinich |
| 4,486,680 A | 12/1984 | Bonnet et al. |
| 4,505,767 A | 3/1985 | Quin |

(Continued)

FOREIGN PATENT DOCUMENTS

| | | |
|---|---|---|
| DE | 2256127 | 5/1974 |
| DE | 3821836 A1 | 2/1976 |

(Continued)

OTHER PUBLICATIONS

"E-Beam Theory" RDI-IBA Technology Group, downloaded from web on Oct. 8, 2002 <http://www.e-beam-rd/Ebeam Theory.htm> 2 pages total.

(Continued)

*Primary Examiner* — Julian W Woo
(74) *Attorney, Agent, or Firm* — Knobbe Martens Olson & Bear LLP (57) ABSTRACT

Ultrasound catheter devices and methods provide enhanced disruption of blood vessel obstructions. Ultrasound catheter devices generally include an elongate flexible catheter body with one or more lumens, an ultrasound transmission member extending longitudinally through the catheter body lumen and a distal head coupled with the transmission member and positioned adjacent the distal end of the catheter body for disrupting occlusions. Improved features of ultrasound catheters include catheter bodies and ultrasound transmission members with increasing distal flexibility, guidewire tubes allowing contact between a guidewire and an ultrasound transmission member, distal heads with improved guidewire lumens, and torquable proximal housings for enhancing disruption of blood vessel occlusions.

20 Claims, 9 Drawing Sheets

(56) References Cited

U.S. PATENT DOCUMENTS

| | | |
|---|---|---|
| 4,565,589 A | 1/1986 | Harrison |
| 4,572,184 A | 2/1986 | Stohl et al. |
| 4,664,112 A | 5/1987 | Kensey et al. |
| 4,665,906 A | 5/1987 | Jervis |
| 4,679,558 A | 7/1987 | Kensey et al. |
| 4,700,705 A | 10/1987 | Kensey et al. |
| 4,721,117 A | 1/1988 | Mar et al. |
| 4,750,902 A | 6/1988 | Wuchinich et al. |
| 4,808,153 A | 2/1989 | Parisi |
| 4,811,743 A | 3/1989 | Stevens |
| 4,827,911 A | 5/1989 | Broadwin et al. |
| 4,838,853 A | 6/1989 | Parisi |
| 4,854,325 A | 8/1989 | Stevens |
| 4,870,953 A | 10/1989 | DonMichael et al. |
| 4,886,060 A | 12/1989 | Wiksell |
| 4,920,954 A | 5/1990 | Alliger et al. |
| 4,923,462 A | 5/1990 | Stevens |
| 4,924,863 A | 5/1990 | Sterzer |
| 4,931,047 A | 6/1990 | Broadwin et al. |
| 4,936,281 A | 6/1990 | Stasz |
| 4,936,845 A | 6/1990 | Stevens |
| 5,000,185 A | 3/1991 | Yock |
| 5,015,227 A | 5/1991 | Broadwin et al. |
| 5,026,384 A | 6/1991 | Farr et al. |
| 5,046,503 A | 9/1991 | Schneiderman |
| 5,053,008 A * | 10/1991 | Bajaj ............................ 604/104 |
| 5,058,570 A | 10/1991 | Idemoto et al. |
| 5,076,276 A | 12/1991 | Sakurai |
| 5,091,205 A | 2/1992 | Fan |
| 5,100,423 A | 3/1992 | Fearnot |
| 5,109,859 A | 5/1992 | Jenkins |
| 5,114,414 A | 5/1992 | Buchbinder |
| 5,116,350 A | 5/1992 | Stevens |
| 5,127,917 A | 7/1992 | Niederhauser et al. |
| 5,156,143 A | 10/1992 | Bocquet et al. |
| 5,163,421 A | 11/1992 | Bernstein |
| 5,180,363 A | 1/1993 | Idemoto et al. |
| 5,183,470 A | 2/1993 | Wettermann |
| 5,195,955 A | 3/1993 | Don Michael |
| 5,215,614 A | 6/1993 | Wijkamp et al. |
| 5,221,255 A | 6/1993 | Mahurkar et al. |
| 5,226,421 A | 7/1993 | Frisbie et al. |
| 5,234,416 A | 8/1993 | Macaulay et al. |
| 5,238,004 A | 8/1993 | Sahatjian et al. |
| 5,242,385 A | 9/1993 | Strukel |
| 5,243,997 A | 9/1993 | Uflacker et al. |
| 5,248,296 A | 9/1993 | Alliger |
| 5,255,669 A | 10/1993 | Kubota et al. |
| 5,267,954 A | 12/1993 | Nita |
| 5,269,291 A | 12/1993 | Carter |
| 5,269,297 A | 12/1993 | Weng et al. |
| 5,269,793 A | 12/1993 | Simpson |
| 5,287,858 A | 2/1994 | Hammerslag et al. |
| 5,290,229 A | 3/1994 | Paskar |
| 5,304,115 A | 4/1994 | Pflueger |
| 5,304,131 A | 4/1994 | Paskar |
| 5,312,328 A | 5/1994 | Nita et al. |
| 5,324,255 A | 6/1994 | Passafaro et al. |
| 5,324,260 A | 6/1994 | O'neill et al. |
| 5,325,860 A | 7/1994 | Seward et al. |
| 5,326,342 A | 7/1994 | Pflueger et al. |
| 5,341,818 A | 8/1994 | Abrams et al. |
| 5,342,292 A | 8/1994 | Nita et al. |
| 5,344,395 A | 9/1994 | Whalen et al. |
| 5,346,502 A | 9/1994 | Estabrook et al. |
| 5,362,309 A | 11/1994 | Carter |
| 5,368,557 A | 11/1994 | Nita et al. |
| 5,368,558 A | 11/1994 | Nita |
| 5,376,084 A | 12/1994 | Bacich et al. |
| 5,378,234 A | 1/1995 | Hammerslag et al. |
| 5,380,274 A | 1/1995 | Nita |
| 5,380,316 A | 1/1995 | Aita et al. |
| 5,382,228 A | 1/1995 | Nita et al. |
| 5,383,460 A | 1/1995 | Jang et al. |
| 5,389,096 A | 2/1995 | Aita et al. |
| 5,397,293 A | 3/1995 | Alliger et al. |
| 5,397,301 A | 3/1995 | Pflueger et al. |
| 5,405,318 A | 4/1995 | Nita |
| 5,409,483 A | 4/1995 | Campbell et al. |
| 5,417,672 A | 5/1995 | Nita et al. |
| 5,417,703 A | 5/1995 | Brown et al. |
| 5,427,118 A | 6/1995 | Nita et al. |
| 5,431,168 A | 7/1995 | Webster, Jr. |
| 5,431,663 A | 7/1995 | Carter |
| 5,443,078 A | 8/1995 | Uflacker |
| 5,447,509 A | 9/1995 | Mills et al. |
| 5,449,369 A | 9/1995 | Imran |
| 5,451,209 A | 9/1995 | Ainsworth et al. |
| 5,465,733 A | 11/1995 | Hinohara et al. |
| 5,474,531 A | 12/1995 | Carter |
| 5,480,379 A | 1/1996 | La Rosa |
| 5,484,398 A | 1/1996 | Stoddard |
| 5,487,757 A | 1/1996 | Truckai et al. |
| 5,507,738 A | 4/1996 | Ciervo |
| 5,516,043 A | 5/1996 | Manna et al. |
| 5,527,273 A | 6/1996 | Manna et al. |
| 5,540,656 A | 7/1996 | Pflueger et al. |
| 5,542,917 A | 8/1996 | Nita et al. |
| 5,597,882 A | 1/1997 | Schiller et al. |
| 5,607,421 A | 3/1997 | Jeevanandam et al. |
| 5,611,807 A | 3/1997 | O'Boyle |
| 5,618,266 A | 4/1997 | Liprie |
| 5,626,593 A | 5/1997 | Imran |
| 5,658,282 A | 8/1997 | Daw et al. |
| 5,695,460 A | 12/1997 | Siegel et al. |
| 5,695,507 A | 12/1997 | Auth et al. |
| 5,715,825 A | 2/1998 | Crowley |
| 5,720,724 A | 2/1998 | Ressemann et al. |
| 5,728,062 A | 3/1998 | Brisken |
| 5,738,100 A | 4/1998 | Yagami et al. |
| 5,797,876 A | 8/1998 | Spears et al. |
| 5,816,923 A | 10/1998 | Milo et al. |
| 5,827,203 A | 10/1998 | Nita |
| 5,830,222 A | 11/1998 | Makower |
| 5,895,397 A | 4/1999 | Jang et al. |
| 5,902,287 A | 5/1999 | Martin |
| 5,904,667 A | 5/1999 | Falwell |
| 5,916,192 A | 6/1999 | Nita et al. |
| 5,935,142 A | 8/1999 | Hood |
| 5,935,144 A | 8/1999 | Estabrook |
| 5,944,737 A | 8/1999 | Tsonton et al. |
| 5,957,882 A | 9/1999 | Nita et al. |
| 5,957,899 A | 9/1999 | Spears et al. |
| 5,964,223 A | 10/1999 | Baran |
| 5,967,984 A | 10/1999 | Chu et al. |
| 5,971,949 A | 10/1999 | Levin et al. |
| 5,976,119 A | 11/1999 | Spears et al. |
| 5,989,208 A | 11/1999 | Nita |
| 5,997,497 A | 12/1999 | Nita et al. |
| 6,004,280 A | 12/1999 | Buck et al. |
| 6,007,499 A | 12/1999 | Martin et al. |
| 6,007,514 A | 12/1999 | Nita |
| 6,029,671 A | 2/2000 | Stevens et al. |
| 6,030,357 A | 2/2000 | Daoud et al. |
| 6,051,010 A | 4/2000 | DiMatteo et al. |
| 6,113,558 A | 9/2000 | Rosenschein et al. |
| 6,123,698 A | 9/2000 | Spears et al. |
| 6,149,596 A | 11/2000 | Bancroft |
| 6,159,176 A | 12/2000 | Broadwin et al. |
| 6,165,127 A | 12/2000 | Crowley |
| 6,165,188 A | 12/2000 | Saadat et al. |
| 6,179,809 B1 * | 1/2001 | Khairkhahan et al. ..... 604/95.04 |
| 6,190,353 B1 | 2/2001 | Makower et al. |
| 6,206,842 B1 | 3/2001 | Tu et al. |
| 6,210,356 B1 | 4/2001 | Anderson et al. |
| 6,217,543 B1 | 4/2001 | Anis et al. |
| 6,231,546 B1 | 5/2001 | Milo et al. |
| 6,231,587 B1 | 5/2001 | Makower |
| 6,235,007 B1 | 5/2001 | Divino, Jr. et al. |
| 6,241,692 B1 | 6/2001 | Tu et al. |
| 6,241,703 B1 | 6/2001 | Levin et al. |
| 6,277,084 B1 | 8/2001 | Abele et al. |
| 6,283,983 B1 | 9/2001 | Makower et al. |
| 6,287,271 B1 | 9/2001 | Dubrul et al. |

(56) References Cited

U.S. PATENT DOCUMENTS

| | | |
|---|---|---|
| 6,287,285 B1 | 9/2001 | Michal et al. |
| 6,287,317 B1 | 9/2001 | Makower et al. |
| 6,296,620 B1 | 10/2001 | Gesswein et al. |
| 6,302,875 B1 | 10/2001 | Makower et al. |
| 6,315,741 B1 | 11/2001 | Martin et al. |
| 6,379,378 B1 | 4/2002 | Werneth et al. |
| 6,387,109 B1 | 5/2002 | Davison et al. |
| 6,394,956 B1 | 5/2002 | Chandrasekaran et al. |
| 6,398,736 B1 | 6/2002 | Seward |
| 6,416,533 B1 | 7/2002 | Gobin et al. |
| 6,423,026 B1 | 7/2002 | Gesswein et al. |
| 6,433,464 B2 | 8/2002 | Jones |
| 6,450,975 B1 * | 9/2002 | Brennan et al. ............... 600/585 |
| 6,454,757 B1 | 9/2002 | Nita et al. |
| 6,454,997 B1 | 9/2002 | Divino, Jr. et al. |
| 6,491,707 B2 | 12/2002 | Makower |
| 6,494,891 B1 | 12/2002 | Cornish et al. |
| 6,508,781 B1 | 1/2003 | Brennan et al. |
| 6,508,784 B1 | 1/2003 | Shu |
| 6,511,458 B2 | 1/2003 | Milo et al. |
| 6,524,251 B2 | 2/2003 | Rabiner et al. |
| 6,544,215 B1 | 4/2003 | Bencini et al. |
| 6,547,754 B1 | 4/2003 | Evans et al. |
| 6,551,337 B1 | 4/2003 | Rabiner et al. |
| 6,554,846 B2 | 4/2003 | Hamilton et al. |
| 6,558,502 B2 | 5/2003 | Divino, Jr. et al. |
| 6,562,031 B2 | 5/2003 | Chandrasekaran et al. |
| 6,589,253 B1 | 7/2003 | Cornish et al. |
| 6,596,235 B2 | 7/2003 | Divino, Jr. et al. |
| 6,616,617 B1 | 9/2003 | Ferrera et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,750 B2 | 3/2004 | Yock |
| 6,719,725 B2 | 4/2004 | Milo et al. |
| 6,733,451 B2 | 5/2004 | Rabiner et al. |
| 6,761,698 B2 | 7/2004 | Shibata et al. |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 7,004,173 B2 | 2/2006 | Sparks et al. |
| 7,056,294 B2 | 6/2006 | Khairkhahan et al. |
| 7,131,983 B2 | 11/2006 | Murakami |
| 7,137,963 B2 | 11/2006 | Nita et al. |
| 7,220,233 B2 | 5/2007 | Nita et al. |
| 7,267,650 B2 | 9/2007 | Chow et al. |
| 7,335,180 B2 | 2/2008 | Nita et al. |
| 7,384,407 B2 | 6/2008 | Rodriguez et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,604,608 B2 | 10/2009 | Nita et al. |
| 8,133,236 B2 | 3/2012 | Nita |
| 2003/0009153 A1 | 1/2003 | Brisken et al. |
| 2003/0036705 A1 | 2/2003 | Hare et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2005/0222557 A1 | 10/2005 | Baxter et al. |
| 2006/0264759 A1 | 11/2006 | Moehring et al. |
| 2007/0037119 A1 | 2/2007 | Pal et al. |
| 2007/0260172 A1 | 11/2007 | Nita |
| 2011/0130834 A1 | 6/2011 | Wilson et al. |

FOREIGN PATENT DOCUMENTS

| | | |
|---|---|---|
| DE | 2438648 A1 | 1/1990 |
| DE | 8910040 | 1/1990 |
| DE | 4042435 | 8/1991 |
| EP | 0005719 | 12/1979 |
| EP | 316789 A2 | 5/1989 |
| EP | 316789 B1 | 5/1989 |
| EP | 0376562 | 7/1990 |
| EP | 0379156 | 7/1990 |
| EP | 0394583 | 10/1990 |
| EP | 0443256 | 8/1991 |
| EP | 0541249 | 5/1993 |
| EP | 0820728 | 1/1998 |
| EP | 1323481 A2 | 7/2003 |
| GB | 1106957 | 3/1968 |
| JP | SHO61-272045 | 12/1986 |
| JP | 01099547 | 4/1989 |
| JP | 2-71510 | 5/1990 |
| JP | U03067608 | 7/1991 |
| JP | 2006086822 | 3/1994 |
| JP | 2007116260 | 5/1995 |
| JP | 10216140 | 8/1998 |
| JP | 2001104356 | 4/2001 |
| JP | 2001321388 | 11/2001 |
| JP | 2002186627 | 7/2002 |
| JP | 2005-253874 | 9/2005 |
| JP | 2006-522644 | 10/2006 |
| WO | WO 87/05739 A1 | 9/1987 |
| WO | WO 89/06515 A1 | 9/1989 |
| WO | WO 90/01300 A1 | 2/1990 |
| WO | WO9004362 | 5/1990 |
| WO | WO9107917 | 6/1991 |
| WO | WO9211815 | 7/1992 |
| WO | WO9308750 | 5/1993 |
| WO | WO9316646 | 9/1993 |
| WO | WO9412140 | 6/1994 |
| WO | WO9414382 | 7/1994 |
| WO | WO9508954 | 4/1995 |
| WO | WO9509571 | 4/1995 |
| WO | WO 95/15192 | 6/1995 |
| WO | WO9635469 | 11/1996 |
| WO | WO 97/21462 | 6/1997 |
| WO | WO9745078 | 12/1997 |
| WO | WO98/35721 | 8/1998 |
| WO | WO 98/52637 | 11/1998 |
| WO | WO9925412 | 5/1999 |
| WO | WO0053341 A1 | 9/2000 |
| WO | WO00/67830 | 11/2000 |
| WO | WO2004012609 | 2/2004 |
| WO | WO 2004/093736 A2 | 11/2004 |
| WO | WO2004112888 | 12/2004 |
| WO | WO 2005/053769 A2 | 6/2005 |
| WO | WO 2006/049593 | 5/2006 |

OTHER PUBLICATIONS

"Irradiation, biological, and other technologies: E-beam, biological, and sharps treatment systems" Chapter 9, Irradiation, Biological, and Other Technologies, pp. 69-74.

"What is electron beam curing?" downloaded from web on Nov. 14, 2002 <http://www.mis.omi.gov/researchgroups/composites/new%20orccmt%20pages/pages/ebwha> 4 pages total.

Calhoun, et al., "Electron-beam systems for medical device sterilization" downloaded from web on Oct. 8, 2002 <http://www.devicelink.com/mpb/archives/97/07/002.html> 7 pages total.

Office Action dated May 20, 2010 from Japanese Application No. 2006-541200 filed on Oct. 25, 2004.

Siegel, et al., "In Vivo Ultrasound Arterial Recanalization of Atherosclerotic Total Occlusions", Journal of the American College of Cardiology, Feb. 1990, vol. 15, No. 2, pp. 345-351.

Extended European Search Report dated Mar. 5, 2012 for European Application No. 12153606.4.

Health Care Without Harm [report], Non-Incineration Medical Waste Treatment Technologies, "Irradiation, biological, and other technologies: E-beam, biological, and sharps treatment systems", Chapter 9., Aug. 2001, pp. 69-74.

Office Action from Japanese Appln No. 2010-181956, Oct. 11, 2012.

* cited by examiner

STEERABLE ULTRASOUND CATHETER

CROSS REFERENCE TO RELATED APPLICATIONS

This application is a divisional of U.S. patent application Ser. No. 10/722,209, filed Nov. 24, 2003, entitled "Steerable Ultrasound Catheter". This application is also related to the following pending U.S. patent applications, the full disclosures of which are all hereby incorporated by reference: U.S. patent application Ser. No. 12/021,082, filed Jan. 28, 2008, entitled "Steerable Ultrasound Catheter"; U.S. patent application Ser. No. 10/229,371, filed Aug. 26, 2002, entitled "Ultrasound Catheter for Disrupting Blood Vessel Obstructions"; U.S. patent application Ser. No. 10/345,078, filed Jan. 14, 2003, entitled "Ultrasound Catheter and Methods for Making and Using Same"; U.S. patent application Ser. No. 10/375,903, filed Feb. 26, 2003, entitled "Ultrasound Catheter Apparatus"; and U.S. patent application Ser. No. 10/410,617, filed Apr. 8, 2003, entitled "Improved Ultrasound Catheter Devices and Methods".

BACKGROUND OF THE INVENTION

The present invention relates generally to medical devices and methods. More specifically, the present invention relates to ultrasound catheter devices and methods for treating occlusive intravascular lesions.

Catheters employing various types of ultrasound transmitting members have been successfully used to ablate or otherwise disrupt obstructions in blood vessels. Specifically, ablation of atherosclerotic plaque or thromboembolic obstructions from peripheral blood vessels such as the femoral arteries has been particularly successful. Various ultrasonic catheter devices have been developed for use in ablating or otherwise removing obstructive material from blood vessels. For example, U.S. Pat. Nos. 5,267,954 and 5,380,274, issued to an inventor of the present invention and hereby incorporated by reference, describe ultrasound catheter devices for removing occlusions. Other examples of ultrasonic ablation devices for removing obstructions from blood vessels include those described in U.S. Pat. Nos. 3,433,226 (Boyd), 3,823,717 (Pohlman, et al.), 4,808,153 (Parisi), 4,936,281 (Stasz), 3,565,062 (Kuris), 4,924,863 (Sterzer), 4,870,953 (Don Michael, et al), and 4,920,954 (Alliger, et al.), as well as other patent publications WO87-05739 (Cooper), WO89-06515 (Bernstein, et al.), WO90-0130 (Sonic Needle Corp.), EP, EP316789 (Don Michael, et al.), DE3, 821,836 (Schubert) and DE2438648 (Pohlman). While many ultrasound catheters have been developed, however, improvements are still being pursued.

Typically, an ultrasonic catheter system for ablating occlusive material includes three basic components: an ultrasound generator, an ultrasound transducer, and an ultrasound catheter. The generator converts line power into a high frequency current that is delivered to the transducer. The transducer contains piezoelectric crystals which, when excited by the high frequency current, expand and contract at high frequency. These small, high-frequency expansions (relative to an axis of the transducer and the catheter) are amplified by the transducer horn into vibrational energy. The vibrations are then transmitted from the transducer through the ultrasound catheter via an ultrasound transmission member (or wire) running longitudinally through the catheter. The transmission member transmits the vibrational energy to the distal end of the catheter where the energy is used to ablate or otherwise disrupt a vascular obstruction.

To effectively reach various sites for treatment of intravascular occlusions, ultrasound catheters of the type described above typically have lengths of about 150 cm or longer. To permit the advancement of such ultrasound catheters through small and/or tortuous blood vessels such as the aortic arch, coronary vessels, and peripheral vasculature of the lower extremities, the catheters (and their respective ultrasound transmission wires) must typically be sufficiently small and flexible. Also, due to attenuation of ultrasound energy along the long, thin, ultrasound transmission wire, a sufficient amount of vibrational energy must be applied at the proximal end of the wire to provide a desired amount of energy at the distal end.

A number of ultrasound catheter devices have been described, for example in U.S. patent application Ser. Nos. 10/229,371, 10/345,078, 10/375,903, and 10/410,617, which were previously incorporated by reference. Improvements, however, are always being sought. For example, it continues to be challenging to develop a catheter that is stiff enough to be pushable or "steerable" through vasculature yet flexible enough, at least along part of its length, to navigate small, tortuous blood vessels, such as the coronary arteries or tortuous peripheral vasculature. It is also sometimes difficult to manipulate currently available ultrasound catheter devices, for example to twist or torque the proximal end of the catheter to move the distal end in a way that helps with navigation through the vasculature. Passage of a guidewire through an ultrasound catheter may also be improved upon, such that the guidewire does not interfere with, and may even enhance, disruption of vascular occlusions.

Therefore, a need exists for improved ultrasound catheter devices and methods that provide ablation or disruption of vascular occlusions. Ideally, such ultrasound catheters would have enhanced ability to navigate through small, tortuous blood vessels such as the coronary arteries. It would also be advantageous to have catheters that could be easily manipulated by a user. Ideally, such devices would allow for passage of a guidewire without interfering with, and perhaps even enhancing, disruption of vascular occlusions. At least some of these objectives will be met by the present invention.

BRIEF SUMMARY OF THE INVENTION

Ultrasound catheter devices and methods provide enhanced disruption of blood vessel obstructions. Generally, ultrasound catheters include an elongate flexible catheter body with one or more lumens, an ultrasound transmission member extending longitudinally through the catheter body lumen, and a distal head coupled with the transmission member and positioned adjacent the distal end of the catheter body for disrupting occlusions. Improved features include but are not limited to catheter bodies and ultrasound transmission members with increasing flexibility toward their distal ends, devices that bend concomitantly with one or more bends in a guidewire and/or a blood vessel, a proximal housing coupled with an ultrasound catheter body for enhancing manipulation of the catheter body, a guidewire lumen configured to allow contact between a guidewire and an ultrasound transmission member, distal heads with improved guidewire lumens and the like.

In one aspect of the present invention, an ultrasound catheter for disrupting occlusions in blood vessels is provided, which can be guided from an access site on a patient's body to a target site adjacent an occlusion. The ultrasound catheter generally includes an elongate flexible catheter body, an ultrasound transmission member extending longitudinally through the lumen of the catheter body, a distal head coupled with the distal end of the ultrasound transmission member and disposed adjacent the distal end of the catheter body, and at least one coupling member for coupling the ultrasound transmission member with a source of ultrasound energy. The catheter body has a proximal portion, a distal portion and at least one lumen, the proximal portion being stiffer than the distal portion, and the distal portion being more flexible near the distal end of the catheter body than near the proximal portion of the catheter body. The ultrasound transmission member has a proximal end and a distal end and is more flexible near its distal end than near its proximal end. Thus, both the distal portion of the catheter body and the ultrasound transmission member are more flexible toward the distal end of the device.

The increasing flexibility of the catheter body and the ultrasound transmission wire toward the distal end of the catheter device may be achieved by any suitable fabrication method. In some embodiments, for example, the ultrasound transmission wire, catheter body, or both may be tapered, such that their cross-sectional diameters decrease distally. In one embodiment, for example, the cross-sectional diameter of a catheter body may range from between about 0.102 cm and about 0.178 cm along its proximal end to between about 0.076 cm and about 0.127 cm along its distal end, and the cross-sectional diameter of an ultrasound transmission member may range from between about 0.051 cm and about 0.102 cm near its proximal end to between about 0.013 cm and about 0.038 cm near its distal end. Additionally or alternatively, the wall thickness of the catheter body may decrease from proximal to distal. For example, in one embodiment, the wall thickness of a catheter body may measure about 0.007 cm to about 0.020 cm along its proximal portion and about 0.005 cm to about 0.013 cm along its distal portion. In these or other embodiments, various combinations of materials may be used to give the catheter body, transmission wire or both a desired flexibility profile. Providing an ultrasound catheter with a catheter body and ultrasound transmission wire that both increase in flexibility toward the distal end of the device will enhance navigation of the distal end of the device through tortuous blood vessels. In one embodiment, for example, the distal portion of the device will be sufficiently flexible to pass, without kinking, through at least 5 cm length of a blood vessel having at least one bend and an inner diameter of between about 2 mm and about 5 mm. A "tortuous vessel," for the purposes of this application, means having at least one bend or curve, and the bend or curve may have any angle or radius of curvature. In some embodiments, for example, at least one bend in a vessel may have a radius of about 1.0 cm or less. In some instances, of course, a tortuous blood vessel will have multiple bends or curves.

In another aspect of the invention, an ultrasound catheter for disrupting occlusions in blood vessels which can be guided along a guidewire from an access site on a patient's body to a target site adjacent an occlusion includes an elongate flexible catheter body, an ultrasound transmission member extending longitudinally through the lumen of the catheter body, a distal head coupled with the distal end of the ultrasound transmission member and disposed adjacent the distal end of the catheter body, and at least one coupling member for coupling the ultrasound transmission member with a source of ultrasound energy. In this aspect, the catheter body has a proximal portion, a distal portion and at least one lumen, the proximal portion has a larger cross-sectional diameter than the distal portion, the proximal portion is sufficiently stiff to push the distal portion through a blood vessel having at least one bend, and the distal portion is sufficiently flexible to pass through the bend in the blood vessel. The ultrasound transmission member has a proximal end and a distal end, the cross-sectional diameter of the ultrasound transmission member is less near its distal end than near its proximal end, and a distal portion of the ultrasound transmission member is sufficiently flexible to pass through the bend in the blood vessel. Again, in some embodiments the wall of the catheter body may be thinner along the distal portion than along the proximal portion.

In another aspect of the present invention, an ultrasound catheter for disrupting occlusions in blood vessels which can be guided from an access site on a patient's body to a target site adjacent an occlusion includes an elongate flexible catheter body having a proximal portion, a distal portion and at least one lumen, an ultrasound transmission member extending longitudinally through the lumen of the catheter body, a distal head coupled with the distal end of the ultrasound transmission member and disposed adjacent the distal end of the catheter body, and at least one coupling member for coupling the ultrasound transmission member with a source of ultrasound energy. In this aspect, the distal portion of the catheter body is more flexible near a distal end of the catheter body than near the proximal portion of the catheter body, and the ultrasound transmission member is more flexible near its distal end than near its proximal end. Additionally, the distal portion of the catheter body and the ultrasound transmission member are sufficiently flexible to conform concomitantly with at least one bend in a guidewire extended through the at least one lumen.

By "conforming concomitantly" it is meant that the catheter body and the ultrasound transmission member conform to the at least one bend in the guidewire such that the catheter body, transmission member and guidewire bend at an approximately similar angle. In some embodiments, the distal portion of the catheter body and the ultrasound transmission wire are sufficiently flexible to conform concomitantly to multiple bends in the guidewire. Also in some embodiments, the distal portion of the catheter body and the ultrasound transmission member are sufficiently flexible to conform concomitantly to multiple bends in a blood vessel. In various embodiments, the catheter may be advanced over a guidewire, a guidewire may be passed through the catheter body, or the catheter body, ultrasound transmission wire and guidewire may be advanced through a blood vessel simultaneously. Thus, in various embodiments, the distal portion of the catheter body, the ultrasound transmission wire and the guidewire may be passed together or sequentially through the multiple bends in the blood vessel while conforming concomitantly to the multiple bends.

In another aspect of the present invention, an ultrasound catheter for disrupting occlusions in blood vessels which can be guided from an access site on a patient's body to a target site adjacent an occlusion includes an elongate flexible catheter body having a proximal portion, a distal portion and at least one lumen, an ultrasound transmission member extending longitudinally through the lumen of the catheter body, a distal head coupled with the distal end of the ultrasound transmission member and disposed adjacent the distal end of the catheter body, and at least one coupling member for coupling the ultrasound transmission member with a source of ultrasound energy. In this aspect, the distal portion of the catheter body has at least one bend, and at least one lumen, the proximal portion of the catheter body is stiffer than the distal portion, and the distal portion is more flexible near a distal end of the catheter body than near the proximal portion of the catheter body. The ultrasound transmission member is more flexible near its distal end than near its proximal end, the ultrasound transmission member conforms to the at least one bend in the distal portion of the catheter body, and the distal portion of the catheter body and the ultrasound transmission member are sufficiently flexible to conform concomitantly to at least one bend in a guidewire.

In still another aspect of the present invention, an ultrasound catheter for disrupting occlusions in blood vessels which can be guided from an access site on a patient's body to a target site adjacent an occlusion includes an elongate flexible catheter body having a proximal portion, a distal portion and at least one lumen, an ultrasound transmission member extending longitudinally through the lumen of the catheter body, a distal head coupled with the distal end of the ultrasound transmission member and disposed adjacent the distal end of the catheter body, and at least one coupling member for coupling the ultrasound transmission member with a source of ultrasound energy. In this aspect, the catheter body includes a guidewire tube disposed within the lumen, and the proximal portion of the body is stiffer than the distal portion. The guidewire tube includes at least one opening within the catheter body for providing contact between a guidewire extending through the guidewire tube and the ultrasound transmission member.

Allowing a guidewire to contact the ultrasound transmission member may facilitate passage of the guidewire into or through a vascular occlusion, by allowing a portion of the ultrasound energy transmitted by the transmission member to be transferred to the guidewire. In various embodiments, the guidewire may contact the transmission member near the proximal end of the catheter device, near the distal end, near the middle, or some combination thereof. In some embodiments, the guidewire tube includes two openings within the catheter body, to allow the transmission member to pass through the tube. Any other configuration for allowing contact between a guidewire and the ultrasound transmission member is also contemplated.

In another aspect of the present invention, an ultrasound catheter for disrupting occlusions in blood vessels which can be guided from an access site on a patient's body to a target site adjacent an occlusion includes an elongate flexible catheter body having a proximal portion, a distal portion and at least one lumen, an ultrasound transmission member extending longitudinally through the lumen of the catheter body, a distal head coupled with the distal end of the ultrasound transmission member and disposed adjacent the distal end of the catheter body, and at least one coupling member for coupling the ultrasound transmission member with a source of ultrasound energy. In this aspect, the distal head includes a guidewire aperture in the center of its distal end and a guidewire lumen extending through the distal head. The guidewire lumen, in turn, has a different longitudinal axis than the longitudinal axis of the catheter body.

Having a guidewire lumen that exits from the center of the distal head is advantageous for advancing the guidewire as well as the catheter device. Angling the guidewire lumen away from the longitudinal axis of the catheter body allows a guidewire and the ultrasound transmission member to pass through a narrower catheter body, thus decreasing the diameter of the catheter device and facilitating passage through tortuous vessels. In some embodiments, the guidewire lumen in the distal head includes a cavity in which a distal end of a guidewire tube of the catheter body is disposed. In some embodiments, the cavity extends through the distal end of the distal head, such that the distal end of the guidewire tube is flush with the distal end of the distal head. In other embodiments, the cavity extends partially through the distal head, such that the distal end of the guidewire tube is disposed proximal to the distal end of the distal head.

In another aspect of the present invention, an ultrasound catheter for disrupting occlusions in blood vessels which can be guided from an access site on a patient's body to a target site adjacent an occlusion includes an elongate flexible catheter body having a proximal portion, a distal portion and at least one lumen, an ultrasound transmission member extending longitudinally through the lumen of the catheter body, a distal head coupled with the distal end of the ultrasound transmission member and disposed adjacent the distal end of the catheter body, and at least one coupling member for coupling the ultrasound transmission member with a source of ultrasound energy. In this aspect of the invention, the at least one coupling member comprises a housing fixedly coupled with the proximal end of the catheter body such that torque applied to the housing is transmitted along the catheter body to its distal portion.

In yet another aspect of the invention, a method for disrupting an occlusion in a blood vessel involves: advancing an ultrasound catheter through a blood vessel having at least one bend, the catheter conforming concomitantly to the at least one bend, wherein advancing includes contacting an ultrasound transmission member of the ultrasound catheter with a guidewire at one or more locations within the catheter; positioning a distal end of the ultrasound catheter adjacent an occlusion in the blood vessel; and transmitting ultrasound energy to the ultrasound transmission member to disrupt the occlusion into multiple occlusion fragments, wherein transmitting includes transmitting ultrasound energy to the guidewire. Optionally, the method may further include removing at least some of the occlusion fragments from the blood vessel via the ultrasound catheter. In some embodiments, the ultrasound catheter is advanced along the guidewire. Alternatively, the guidewire may be passed through the catheter, or the catheter and the guidewire may be advanced together through the blood vessel. Positioning may also involve advancing the ultrasound catheter and the guidewire along multiple bends in the blood vessel, wherein a catheter body of the catheter, the ultrasound transmission member and the guidewire conform concomitantly to the multiple bends. Bends may have any suitable angle or radius of curvature. In one embodiment, for example, one or more bends may have a radius of about 1.0 cm or less. The method may also involve applying radial force to a proximal housing of the ultrasound catheter to radially turn the distal end of the ultrasound catheter in the blood vessel.

Further aspects and specific embodiments of the invention will be described below, in reference to the attached drawing figures.

DETAILED DESCRIPTION OF THE INVENTION

Ultrasound catheter devices and methods of the present invention generally provide for enhanced treatment of occlusive intravascular lesions. Catheter devices generally include a catheter body, an ultrasound energy transmission member disposed within the catheter body and a distal head coupled with the energy transmission member and disposed adjacent the distal end of the catheter body. The ultrasound transmission member transmits ultrasound energy from an ultrasound transducer to the distal head, causing the head to vibrate and, thus, disrupt vascular occlusions. A number of improved features of such ultrasound catheter devices are described more fully below.

Figure 1:
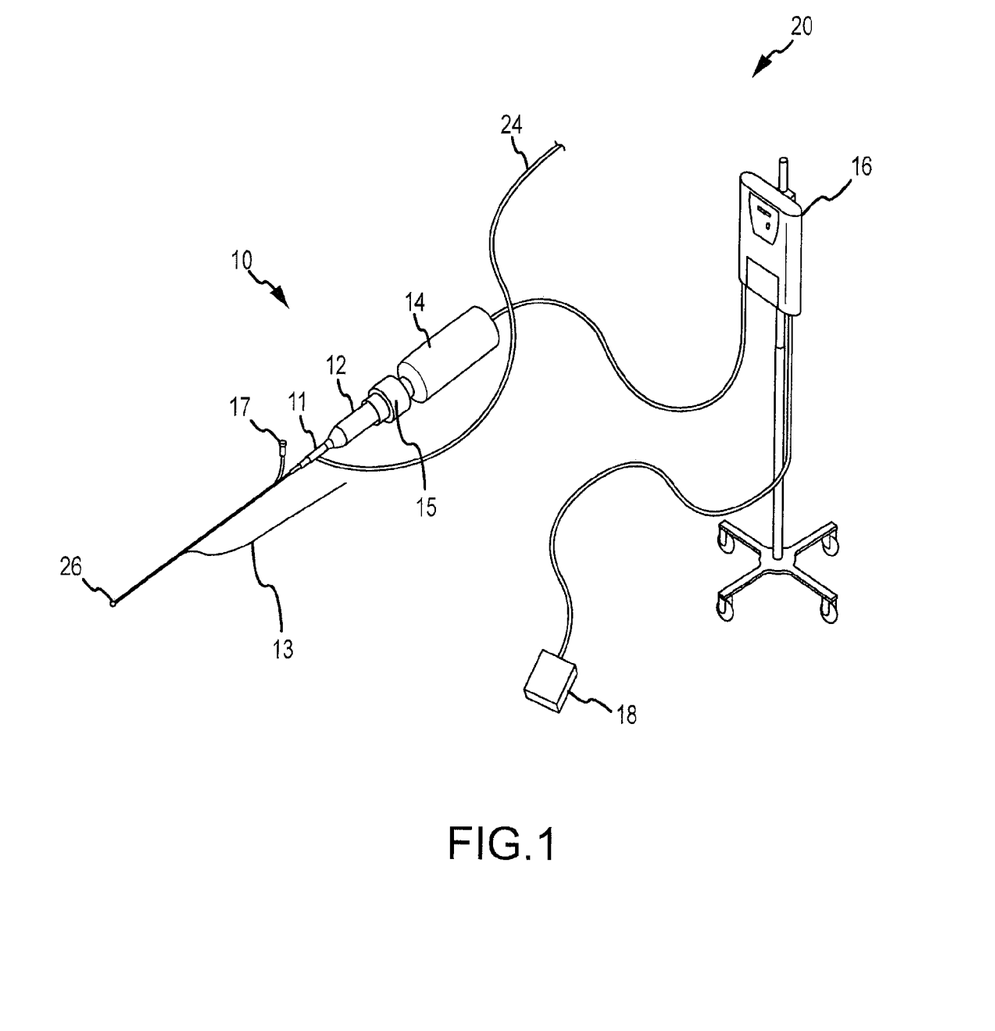
FIG. 1 is a perspective view of an ultrasound catheter system including an ultrasound catheter device and ultrasound energy source according to an embodiment of the present invention.

Referring now to FIG. 1, one embodiment of an ultrasound catheter system 20 suitably includes an ultrasound catheter device 10, including a proximal end connector 12 for coupling device 10 with an ultrasound transducer 14, and an ultrasound generator 16 coupled with transducer 14 and a foot-actuated on/off switch 18 to provide ultrasonic energy to transducer 14 and, thus, to ultrasound catheter 10. Generally, catheter 10 includes an ultrasound transmission member, or wire (not shown), for transmitting energy from the transducer 14 to a distal head 26 of catheter 10. In some embodiments, transducer 14 further includes a securing device 15 for enhancing coupling of catheter 10 to transducer 14. Components of system 20 may be coupled via any suitable means, such as connecting wires of any kind, wireless connections or the like.

In addition to proximal connector 12, ultrasound catheter device 10 may include one or more other various components, such as a Y-connector 11 or the like for providing access for irrigation, guidewire passage, suction or the like. Some embodiments of device include a monorail guidewire 13, some include a proximal guidewire port 17 for over the wire guidewire delivery, and some embodiments include both. In some embodiments, Y-connector may include an irrigation port, for providing access for an irrigation tube 24. Irrigation tube 24, in some embodiments, may be used for introducing one or more fluids, applying vacuum, or both. Generally, catheter device 10 may include any suitable number of sidearms or ports for passage of a guidewire, infusing and/or withdrawing irrigation fluid, dye and/or the like, or any other suitable ports or connections. Also, ultrasound catheters 10 of the present invention may be used with any suitable proximal devices, such as any suitable ultrasound transducer 14, ultrasound generator 16, coupling device(s) and/or the like. Therefore, exemplary FIG. 1 and any following descriptions of proximal apparatus or systems for use with ultrasound catheters 10 should not be interpreted to limit the scope of the present invention as defined in the appended claims.

Figure 1A:
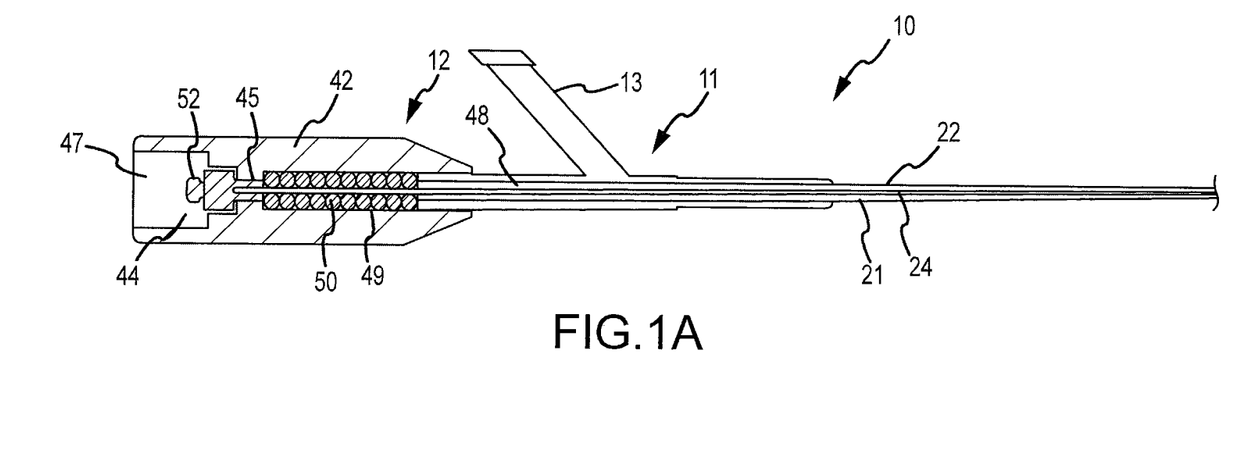
FIG. 1A is a cross-sectional side view of an ultrasound catheter device according to one embodiment of the present invention.

Referring now to FIG. 1A, a cross-sectional side view of one embodiment of ultrasound catheter device 10 is shown. Generally, ultrasound catheter 10 suitably includes an elongate catheter body 22 with an ultrasound transmission member 24 disposed longitudinally through a catheter lumen 21 and ending in distal head (not shown). Catheter body 22 is generally a flexible, tubular, elongate member, having any suitable diameter and length for reaching a vascular occlusion for treatment. In one embodiment, for example, catheter body 22 preferably has an outer diameter of between about 0.5 mm and about 5.0 mm. In other embodiments, as in catheters intended for use in relatively small vessels, catheter body 22 may have an outer diameter of between about 0.25 mm and about 2.5 mm. Catheter body 22 may also have any suitable length. As discussed briefly above, for example, some ultrasound catheters have a length in the range of about 150 cm. However, any other suitable length may be used without departing from the scope of the present invention. Examples of catheter bodies similar to those which may be used in the present invention are described in U.S. Pat. Nos. 5,267,954 and 5,989,208, which were previously incorporated herein by reference.

In some embodiments, catheter body 22 is made from a polymeric material. Sometimes the polymer will have a desired amount of flexibility, such as in one embodiment where catheter body 22 is made of a polymer having a flexural modulus of less than about 160 Psi. In some embodiments, such a polymer will be one of any number of polyether block amides, although other polymers may of course be used. In some embodiments, such polyether block amides may have a Shore D hardness value ranging from about 55 to about 75, while in other embodiments they may have a Shore D hardness value ranging from about 25 to about 55. In some embodiments, the polymeric material includes up to about 5 weight percent of a colorant.

In most embodiments, ultrasound transmission member 24, which may comprise a wire, wave guide or the like, extends longitudinally through catheter body lumen 21 to transmit ultrasonic energy from ultrasound transducer 14 (FIG. 1) to the distal end of catheter 10. Ultrasound transmission member 24 may be formed of any material capable of effectively transmitting ultrasonic energy from ultrasound transducer 14 to the distal end of catheter body 22, including but not limited to metals such as pure titanium or aluminum, or titanium or aluminum alloys. In accordance with one aspect of the invention, all or a portion of ultrasound transmission member 24 may be formed of one or more materials which exhibit superelastic properties. Such material(s) should preferably exhibit superelasticity consistently within the range of temperatures normally encountered by ultrasound transmission member 24 during operation of ultrasound catheter apparatus 10. For example, in some embodiments, the material is an alloy having a tensile strength of between about 170,000 Psi and about 250,000 Psi. In some embodiments, the alloy exhibits elongation of between about 7% and about 17%. For example, in some embodiments the alloy is a nickel-titanium alloy having nickel content of between about 50.50 and about 51.50 atomic weight.

Use of supereleastic metal alloys in ultrasound transmission members is described in U.S. Pat. No. 5,267,954, previously incorporated by reference. Examples of superelastic metal alloys which may be used are described in detail in U.S. Pat. Nos. 4,665,906 (Jervis); 4,565,589 (Harrison); 4,505,767 (Quin); and 4,337,090 (Harrison), the entire disclosures of which are hereby incorporated by reference insofar as they describe the compositions, properties, chemistries and behavior of specific metal alloys which are superelastic within the temperature range at which ultrasound transmission member 24 of the present invention operates, any and all of which superelastic metal alloys may be used to form ultrasound transmission member 24 of the present invention. In some embodiments, for example, the alloy exhibits a superelastic temperature range of about 10 degrees Celsius to about 50 degrees Celsius.

With continued reference to FIG. 1A, one embodiment of proximal end connector 12 suitably includes a housing 42 with a hollow inner bore 44. Bore 44 may have a uniform inner diameter along its length or, alternatively, may have multiple segments, such as a proximal segment 47, a middle segment 45 and a distal segment 49, each of which may surround one or more various components of proximal end connector 12. Generally, proximal segment 47 of bore 44 is configured to allow coupling with ultrasound transducer 14 (not shown) via any suitable coupling means, such as a pressure fit, complementary threads or the like. Proximal segment 47 includes a sonic connector 52 for transmitting vibrational energy from transducer 14 to ultrasound transmission member 24. Sonic connector 52 may be held within housing 42 by any suitable means. In some embodiments, for example, a dowel pin may extend through sonic connector 52 to hold it within housing 42. In another embodiment, sonic connector 52 may be secured within housing 42 by means of a cavity in housing 42.

Middle segment 45 of bore 44, in some embodiments, may surround a portion of sonic connector 52, while in other embodiments, sonic connector 52 may be housed only within proximal segment 47. Sonic connector 52 is coupled with the proximal end of ultrasound transmission member 24 by any suitable means for transmitting ultrasound energy to transmission member 24 from transducer 14. Absorber members 50, such as O-rings, surround a portion of ultrasound transmission member 24 for providing absorption of transverse vibration. Absorber members 50 may be used in any number or combination and have and suitable size and configuration, depending on the desired level of vibration absorption or dampening. Alternatively or additionally, other dampening structures may be used. Thus, the invention is not limited to the combination shown in FIG. 1A.

Distal segment 49 of bore 44 typically surrounds a portion of ultrasound transmission member 24 and may also contain one or more additional sets of absorber members 50. Distal segment 49 may also contain a portion of a Y-connector 11, which is coupled with the distal end of housing 42. Coupling of Y-connector 11 with the distal end of housing 42 may be accomplished via complementary threads, pressure fitting, or any other suitable means. A Y-connector lumen 48 of Y-connector 11 allows passage of ultrasound transmission member 24 and is in fluid communication with catheter body lumen 21.

Generally, pressurized fluid such as a coolant liquid may be infused through a side-arm 13 of Y-connector, through Y-connector lumen 48 and through catheter body lumen 21 so that it flows out of one or more fluid outflow apertures in distal head 26. The temperature and flow rate of such coolant liquid may be specifically controlled to maintain the temperature of ultrasound transmission member 24 at a desired temperature within its optimal working range. In particular, in embodiments of the invention wherein ultrasound transmission member 24 is formed of a metal alloy which exhibits optimal physical properties (e.g. super elasticity) within a specific range of temperatures, the temperature and flow rate of coolant liquid infused through fluid infusion side-arm 13 may be specifically controlled to maintain the temperature of ultrasound transmission member 24 within a range of temperatures at which it demonstrates its most desirable physical properties. For example, in embodiments of the invention wherein ultrasound transmission member 24 is formed of a shape memory alloy which exhibits super elasticity when in its martensite state, but which loses super elasticity as it transitions to an austenite state, it will be desirable to adjust the temperature and flow rate of the coolant liquid infused through fluid infusion side-arm 13 so as to maintain the shape memory alloy of ultrasound transmission member 24 within a temperature range at which the alloy will remain in its martensite state and will not transition to an austenite state. The temperature at which such shape memory alloys transition from a martensite state to an austenite state is known as the "martensite transition temperature" of the material. Thus, in these embodiments, the fluid infused through side-arm 13 will be at such temperature, and will be infused at such rate, as to maintain the shape memory alloy of ultrasound transmission member 24 below its martensite transition temperature.

Figure 2:
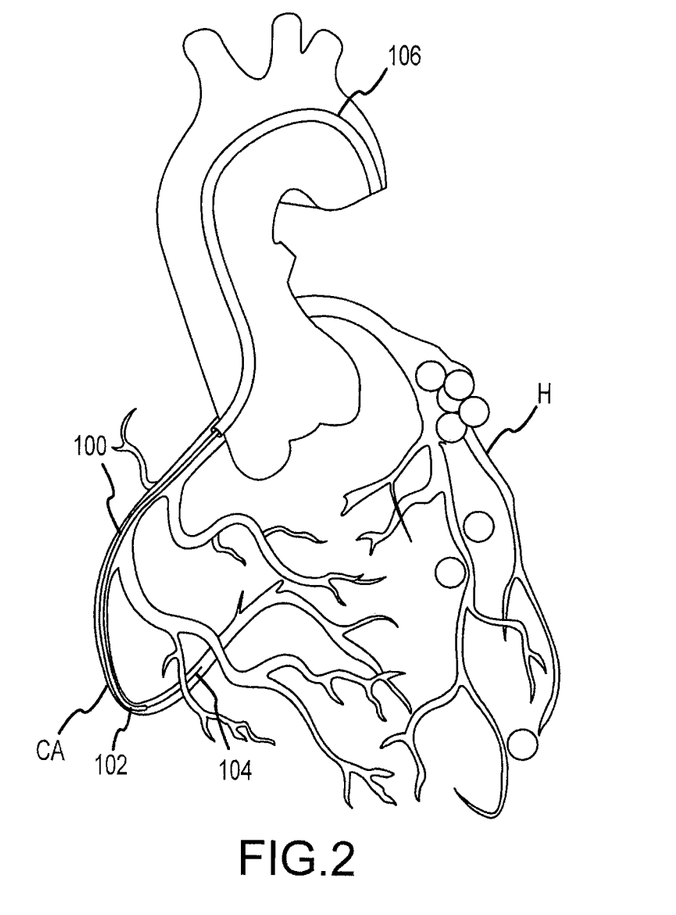
FIG. 2 is a perspective view of a human heart and an ultrasound catheter device, showing one possible path along which a device may advanced according to an embodiment of the present invention.

Referring now to FIG. 2, an ultrasound catheter device 100 may be used in to treat one or more coronary arteries CA in a human heart H. Some embodiments include a flexible distal portion configured to navigate one or more bends 102 in a coronary artery CA or other vessel. In some embodiments, catheter device 100 will be positioned in a coronary artery CA or other vessel by advancing it over (or along with) a guidewire 104. Some embodiments may also include or be used with a guide catheter 106.

As mentioned above, a "tortuous blood vessel," for the purposes of this application, means a vessel having at least one bend (which may also be referred to as a "curve" or the like), having any angle of curvature. In some cases, of course, tortuous vessels also have relatively small inner diameters and multiple bends, and various embodiments of ultrasound catheter device 100 are configured to navigate multiple bends in a vessel. In some embodiments, ultrasound catheter device 100 is configured to conform to one or more bends in a vessel such that two or more components of the device bend concomitantly with one another. For example, in some embodiments, when device 100 extends through a bend in a vessel, an ultrasound transmission member and a catheter body of device 100 will bend with approximately the same angle. In some embodiments, the ultrasound transmission member, the catheter body and a guidewire extending through the catheter may all bend concomitantly to conform to a bend in a blood vessel. Such concomitant bending is in contrast with some prior art devices, wherein the ultrasound transmission member, for example, is relatively stiffer than a distal portion of the catheter body, so that when the device is placed in a bend in a blood vessel, the catheter body bends at a more acute angle than the transmission member.

Figure 3:
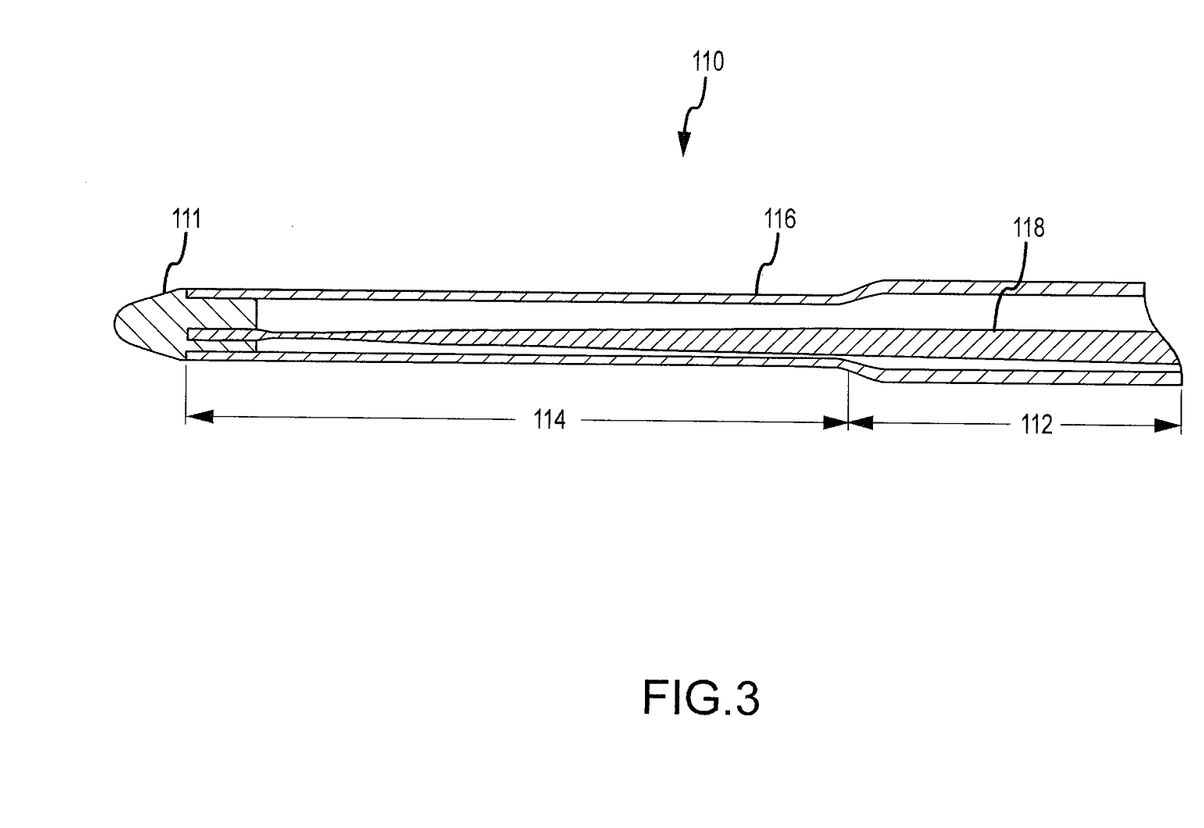
FIG. 3 is a cross-sectional side view of a portion of an ultrasound catheter device according to an embodiment of the present invention.

Referring now to FIG. 3, in one embodiment an ultrasound catheter device 110 of the present invention includes a catheter body 116 having a proximal portion 112 and a distal portion 114, an ultrasound transmission member 118, and a distal head 111. As discussed above, catheter body 116, transmission member 118 and distal head 111 may be fabricated from any suitable material(s) and may have any of a number of suitable configurations, dimensions, and the like. In fact, FIG. 3 is not drawn to scale, and distal portion 114, for example, may be relatively much longer than shown in FIG. 3.

Proximal portion 112 of catheter body 116 is generally stiffer than distal portion 114, such proximal portion 112 is used for pushing or steering, and distal portion 114 is sufficiently flexible to navigate through a tortuous blood vessel to reach an occlusion site. The difference in stiffness/flexibility may be achieved by using different materials for the different portions, by configuring proximal portion 112 with a thicker wall than distal portion 114, by giving proximal portion 112 a larger outer diameter, any combination of these, or any other suitable technique. In some embodiments, proximal portion 112 and distal portion 114 are made from one piece of material, or one extrusion, while in other embodiments two or more pieces of material may be joined together. Ultrasound transmission member 118 also becomes more flexible (less stiff) toward its distal end. This is typically achieved by tapering transmission member 118, and the taper may be gradual, as shown in FIG. 3, or may be achieved in one or more less-gradual steps. By providing catheter body 116 and ultrasound transmission member 118 with progressively increasing flexibility toward the distal end, catheter device 110 may provide enhanced "pushability" or "steerability," while also facilitating navigation of tortuous vessels with distal portion 114.

Figure 4:
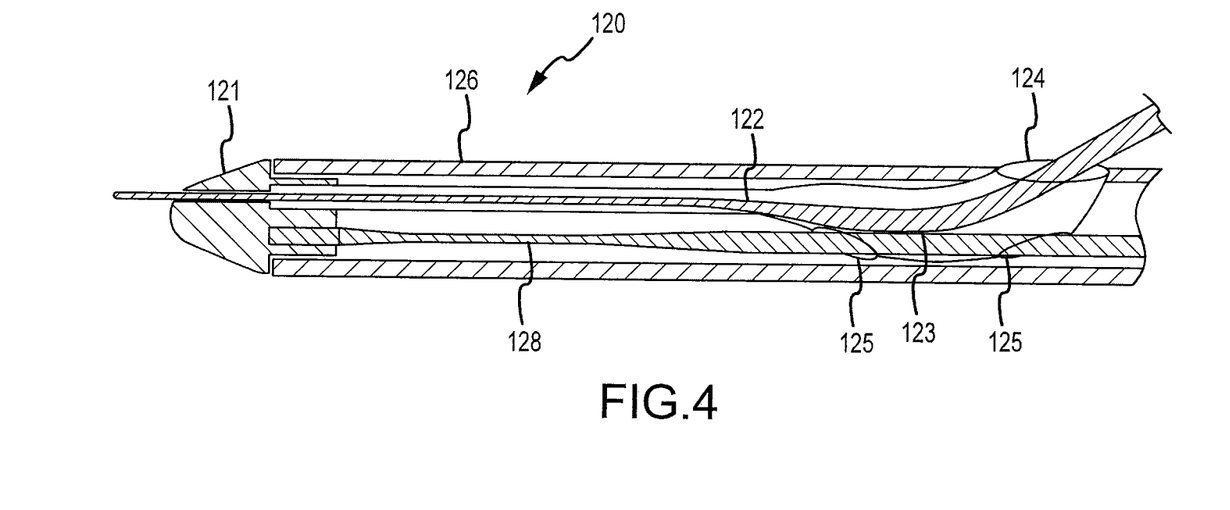
FIG. 4 is a cross-sectional side view of a distal portion of an ultrasound catheter device and a guidewire according to an embodiment of the present invention.

With reference now to FIG. 4, another embodiment of an ultrasound catheter device 120 includes a catheter body 126, an ultrasound transmission member 128 and a guidewire tube 124 disposed within body 126, and a distal head coupled with ultrasound transmission member 121. Guidewire tube 124 may enter catheter body 126 at any suitable location and may extend distally up to, partially through, or completely through distal head 121, as will be explained more fully below. In one embodiment, guidewire tube 124 includes at least one opening 125 disposed within catheter body 126, for allowing a guidewire 122 to contact ultrasound transmission member 128 at one or more locations. In the embodiment shown, guidewire tube 124 includes two openings 125 to allow ultrasound transmission member 128 to pass through tube 124. Any other suitable opening(s) is also contemplated within the scope of the invention. By allowing guidewire 122 to contact ultrasound transmission member 128, an amount of ultrasound energy may be transferred from transmission member 128 to guidewire 122. This transferred energy may cause guidewire 122 to vibrate, and such vibrational energy may enhance the ability of guidewire 122 to cross a vascular occlusion. In many procedures, it is often advantageous to penetrate or cross an occlusion with guidewire 122, and utilizing ultrasound energy transferred to guidewire 122 from transmission member 128 will enhance such procedures.

Figure 5:
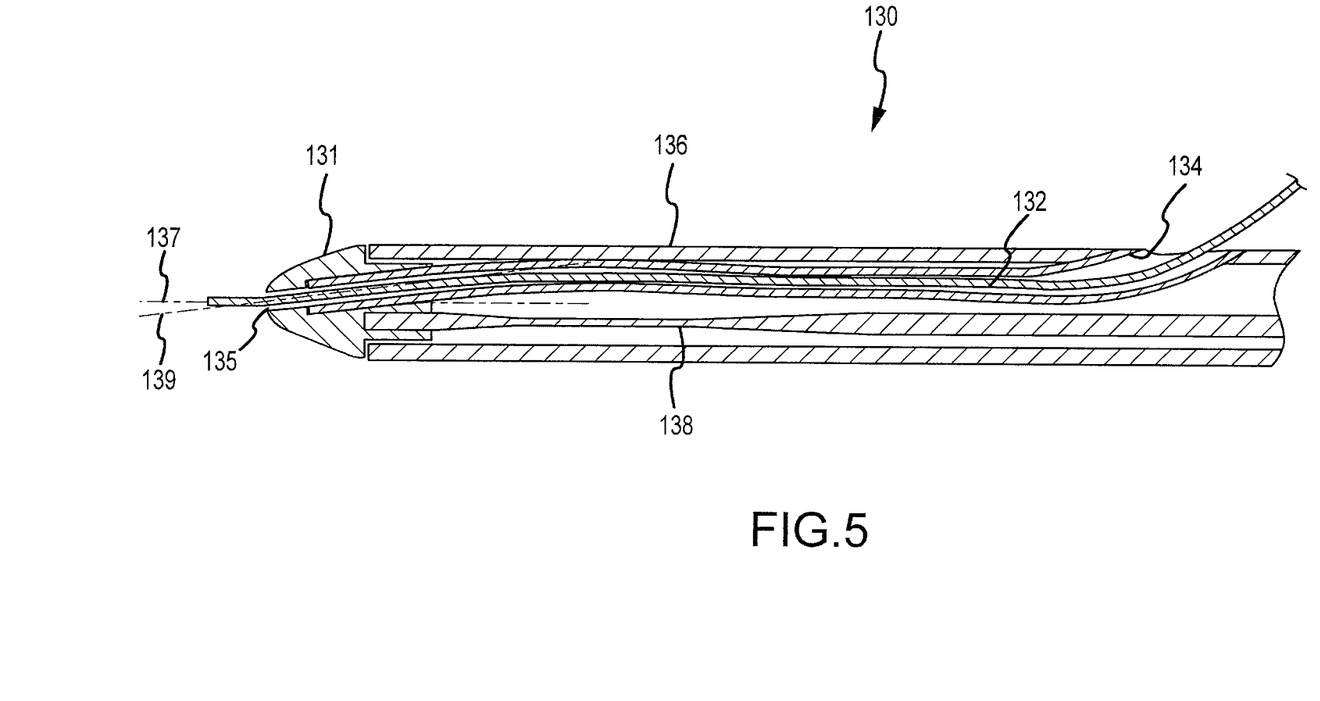
FIG. 5 is a cross-sectional side view of a distal portion of an ultrasound catheter device and a guidewire according to an embodiment of the present invention.
Figure 6:
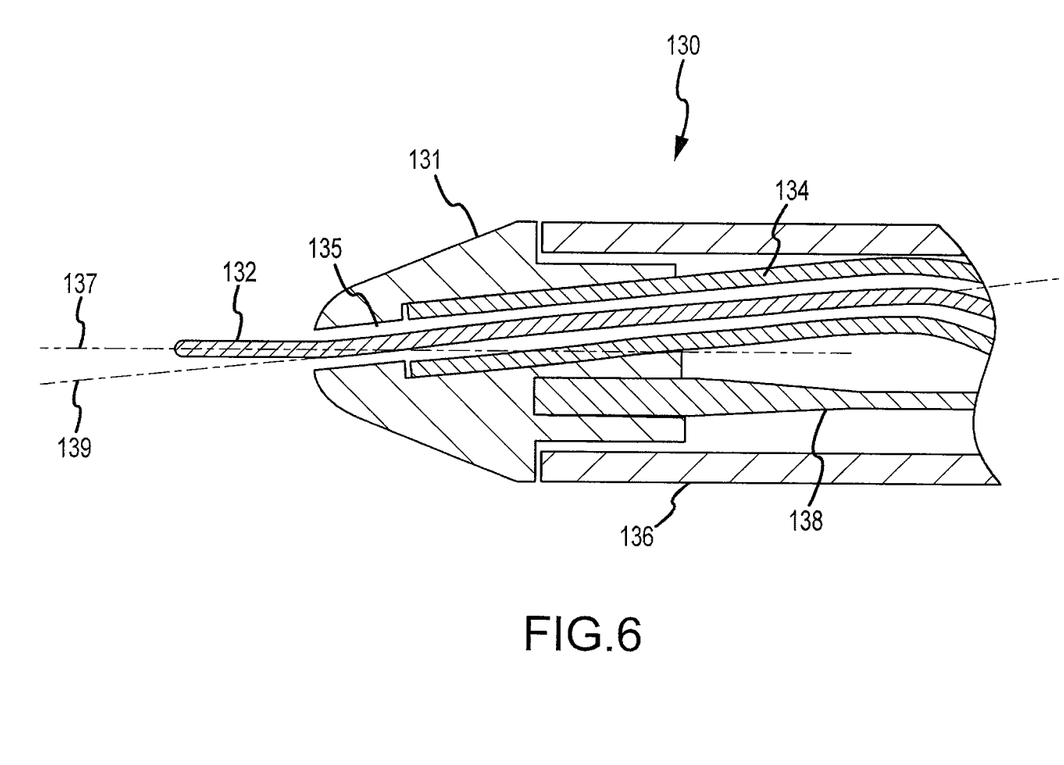
FIG. 6 is a cross-sectional side view of the distal end of the ultrasound catheter device and a guidewire shown in FIG. 5.

Referring now to FIGS. 5 and 6, another embodiment of an ultrasound catheter device 130 suitably includes a catheter body 136, an ultrasound transmission member 138 and a guidewire tube 134 disposed within catheter body 136, and a distal head 131 coupled with the distal ends of transmission member 128 and guidewire tube 134. In this embodiments, distal head 131 includes a guidewire lumen 135. Guidewire lumen 135 has a cavity at its proximal end for accepting the distal end of guidewire tube 134. In alternative embodiments, distal head 131 may not include a cavity, and guidewire tube 134 may abut the proximal end of distal head 131, or the cavity may extend all the way through distal head 131, so that guidewire tube 134 extends all the way through distal head 131 and is flush with the distal end of distal head 131. Also in the embodiment depicted in FIGS. 5 and 6, guidewire lumen 135 of distal head 131 has a longitudinal axis 139 which is not parallel to the overall longitudinal axis 137 of catheter device 130. Thus, at least a distal portion of guidewire tube 134 is also disposed on the longitudinal axis 139 that is not parallel to the catheter device's 130 longitudinal axis 137. At the same time, guidewire lumen 135 of distal head 131 exits approximately at the center of the distal end of distal head 131. Typically, it is advantageous to have guidewire 132 exit approximately the center of distal head 131, to facilitate tracking of catheter device 130 along guidewire 132. It may also be advantageous, however, to offset guidewire tube 134 within catheter body 136, so that guidewire tube 134 and ultrasound transmission member 138 may fit within a catheter body having a smaller inner diameter. Smaller diameter catheters, of course, are more easily advanced through tortuous vasculature.

Generally, any coupled components described above may be coupled by any suitable means, such as adhesives, complementary threaded members, pressure fittings, and the like. For example, distal head 131 may be coupled with ultrasound transmission member 138, guidewire tube 134, and/or catheter body 136 with any suitable adhesive substance or via welding, bonding, pressure fitting, threaded fittings or the like. Adhesives may include, but are not limited to cyanoacrylate (eg. Loctite™, Loctite Corp., Ontario, CANADA or Dron Alpha™, Borden, Inc., Columbus, Ohio) or polyurethane (e.g. Dymax™, Dymax Engineering Adhesive, Torrington, Conn.) adhesives. Some embodiments may also include one or more anchoring members for further securing distal head 131 to the ultrasound catheter device 130. Examples of such anchoring members are described more fully in U.S. patent application Ser. No. 10/410,617, which was previously incorporated by reference.

Figure 7:
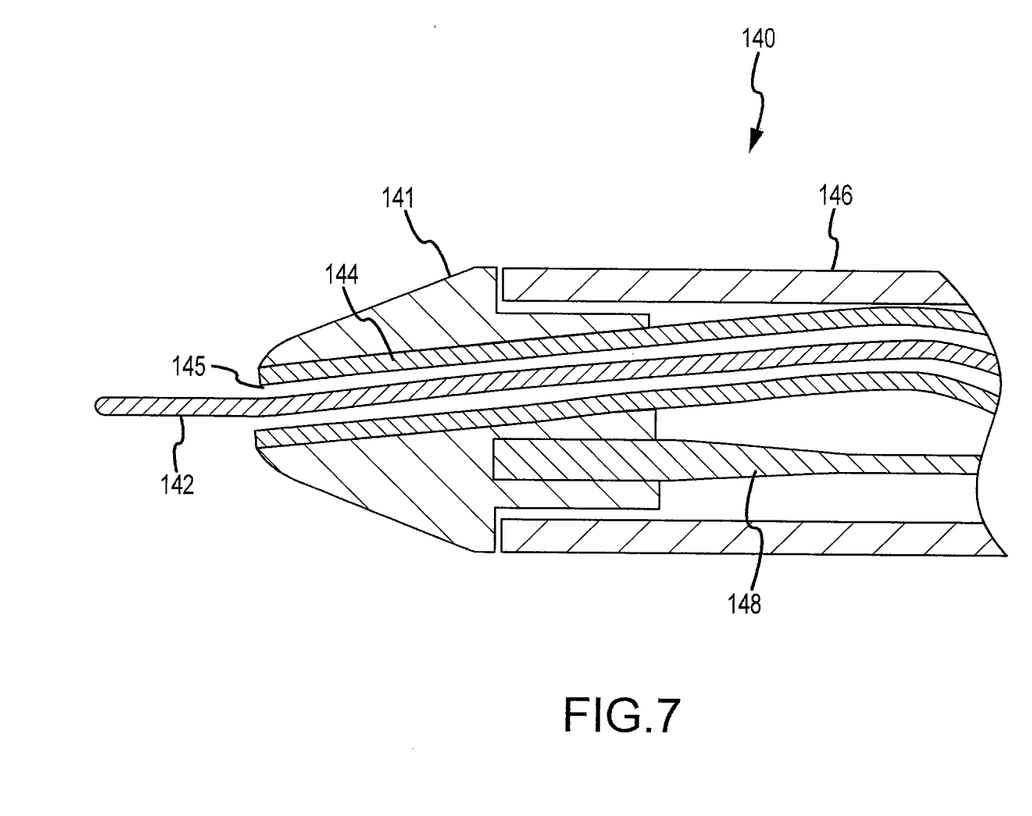
FIG. 7 is a cross-sectional side view of a distal end of an ultrasound catheter device and a guidewire according to an embodiment of the present invention.

Referring now to FIG. 7, another embodiment of an ultrasound catheter device 140 includes a catheter body 146, ultrasound transmission member 148, guidewire tube 144 and distal head 141 having a guidewire lumen 145. In this embodiment, as mentioned briefly above, guidewire lumen 145 is configured such that guidewire tube 144 extends through the whole length of distal head 141 and ends flush with the distal end of distal head 141. Generally, distal head 141 and guidewire lumen 145 may have any suitable sizes, shapes, configurations, dimensions and the like, and the invention is in no way limited by the embodiments shown.

Figure 8:
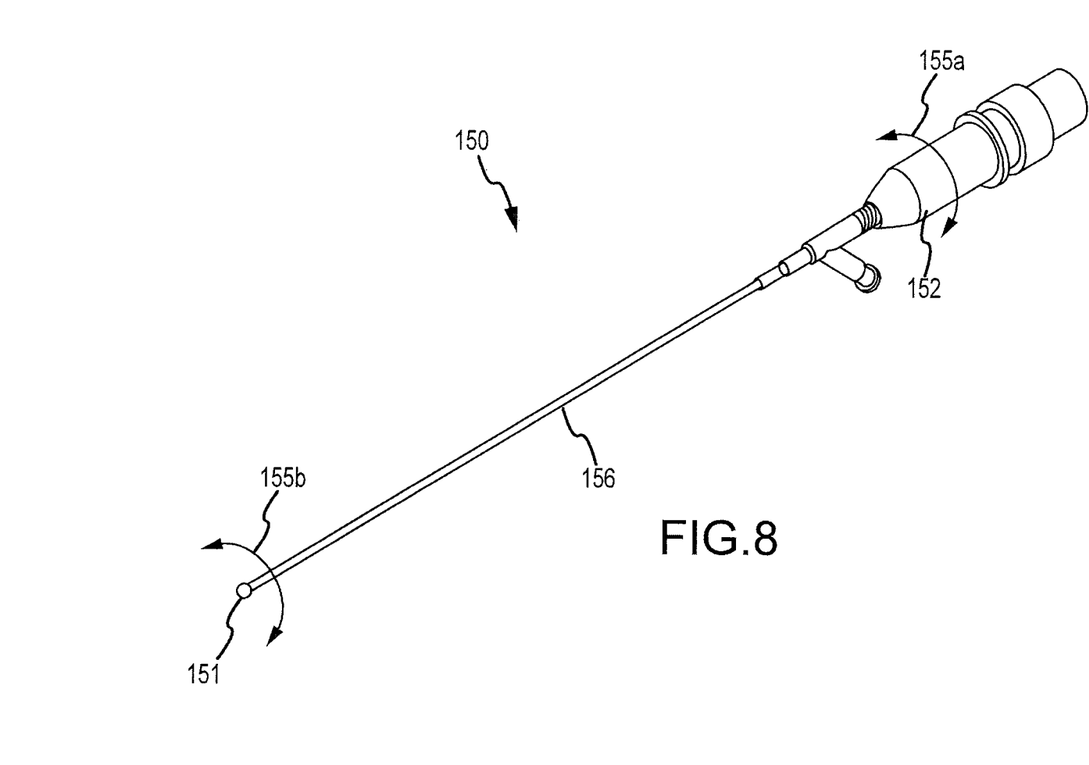
FIG. 8 is a perspective view of an ultrasound catheter device having a fixed proximal housing according to an embodiment of the present invention.

With reference now to FIG. 8, some embodiments of an ultrasound catheter device 150 include a proximal housing 152 that is fixedly coupled with a catheter body 156. Housing 152 may be a handle, a coupling member for coupling the device 150 to an ultrasound transducer, or any other suitable proximal device for allowing a user to manipulate catheter device 150. By providing fixed coupling between housing 152 and catheter body, a proximal rotational force 155a (or torque, or twisting) applied at housing 152 will be transmitted to catheter body 156 to cause the distal end of catheter body 156 and distal head 151 to rotate 155b. It has been found that torquing, twisting or rotating ultrasound catheter device 150 may facilitate navigation of the device through tortuous vasculature and/or dissolution of a vascular occlusion using the device.

Although the invention has been described above with specific reference to various embodiments and examples, it should be understood that various additions, modifications, deletions and alterations may be made to such embodiments without departing from the spirit or scope of the invention. Accordingly, it is intended that all reasonably foreseeable additions, deletions, alterations and modifications be included within the scope of the invention as defined in the following claims.

What is claimed is:

1. A method for disrupting an occlusion in a blood vessel, the method comprising:
providing an ultrasound catheter comprising a catheter body, a distal head, an ultrasound transmission member coupled to the distal head, and a guidewire tube extending through at least a portion of the distal head, the guidewire tube receiving at least a portion of a guidewire and at least a portion of the ultrasound transmission member, the catheter body receiving at least a portion of the guidewire tube and at least a portion of the ultrasound transmission member;

advancing the ultrasound catheter through a blood vessel having at least one bend, the catheter conforming concomitantly to the at least one bend, wherein advancing includes contacting the ultrasound transmission member with the guidewire at one or more locations within the guidewire tube;

positioning the distal head of the ultrasound catheter adjacent an occlusion in the blood vessel; and transmitting ultrasound energy to the ultrasound transmission member to disrupt the occlusion into multiple occlusion fragments, wherein transmitting includes transmitting ultrasound energy to the guidewire.

2. A method as in claim 1, further including removing at least some of the occlusion fragments from the blood vessel via the ultrasound catheter.

3. A method as in claim 1, wherein the ultrasound catheter is advanced along the guidewire.

4. A method as in claim 1, wherein the guidewire is passed through the catheter.

5. A method as in claim 1, wherein the catheter and the guidewire are advanced together through the blood vessel.

6. A method as in claim 1, wherein the ultrasound catheter is advanced through at least one bend having a radius of about 1.0 cm or less.

7. A method as in claim 1, wherein the ultrasound catheter and the guidewire are advanced along multiple bends in the blood vessel, wherein the catheter body of the catheter, the ultrasound transmission member and the guidewire are sufficiently flexible to conform concomitantly to the multiple bends.

8. A method as in claim 1, further comprising applying radial force to a proximal housing of the ultrasound catheter to radially turn the distal head of the ultrasound catheter in the blood vessel.

9. A method for disrupting an occlusion in a blood vessel, the method comprising:

providing an ultrasound catheter comprising a catheter body, a distal head, an ultrasound transmission member coupled to the distal head, and a guidewire tube extending through at least a portion of the distal head, the guidewire tube receiving at least a portion of a guidewire and at least a portion of the ultrasound transmission member, the catheter body receiving at least a portion of the guidewire tube and at least a portion of the ultrasound transmission member;

advancing the ultrasound catheter through a blood vessel;

contacting the ultrasound transmission member with the guidewire at one or more locations within the guidewire tube; and transmitting ultrasound energy from the ultrasound transmission member to the guidewire.

10. A method as in claim 9 further comprising advancing the ultrasound catheter along the guidewire.

11. A method as in claim 9 further comprising extending the guidewire through the catheter.

12. A method as in claim 9 further comprising positioning the distal head of the ultrasound catheter adjacent an occlusion in the blood vessel.

13. A method as in claim 12 further comprising applying radial force to a proximal housing of the ultrasound catheter to rotate the distal head of the ultrasound catheter in the blood vessel.

14. A method for treating a patient:

providing a catheter including an ultrasound transmission member, the catheter having at least a bent configuration and a straight configuration;

providing a guidewire;

advancing the catheter through a blood vessel of the patient; and contacting the guidewire and the ultrasound transmission member at least when the catheter is in the straight configuration and directly transmitting ultrasound energy to the guidewire via the ultrasound transmission member.

15. A method as in claim 14 further comprising advancing the catheter along the guidewire.

16. A method as in claim 14 further comprising extending the guidewire through the catheter.

17. A method as in claim 14 further comprising positioning a distal end of the catheter adjacent an occlusion in the blood vessel.

18. A method for disrupting an occlusion in a blood vessel, the method comprising:

providing a catheter forming a lumen, an ultrasound transmission member and a guidewire being disposed within the lumen;

advancing the catheter through a blood vessel of the patient;

contacting the guidewire and the ultrasound transmission member in the lumen; and penetrating an occlusion with the guidewire using ultrasound energy, the ultrasound energy used to penetrate the occlusion coming directly from the ultrasound transmission member.

19. A method as in claim 18 further comprising advancing the catheter along the guidewire.

20. A method as in claim 18 further comprising extending the guidewire through the catheter.

* * * * *